(12) United States Patent
Bruder et al.

(10) Patent No.: US 7,856,077 B2
(45) Date of Patent: Dec. 21, 2010

(54) CT SCANNER AND METHOD FOR HELICAL SCANNING OF AN EXAMINATION OBJECT WHICH HAS AT LEAST ONE PORTION UNDERGOING PERIODIC MOTION

(75) Inventors: Herbert Bruder, Höchstadt (DE); Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 98 days.

(21) Appl. No.: 12/292,462

(22) Filed: Nov. 19, 2008

(65) Prior Publication Data

US 2009/0141855 A1 Jun. 4, 2009

(30) Foreign Application Priority Data

Nov. 23, 2007 (DE) ........................ 10 2007 056 801

(51) Int. Cl.
*G01N 23/00* (2006.01)
(52) U.S. Cl. ............................................. 378/8; 378/9
(58) Field of Classification Search ................ 378/4–20
See application file for complete search history.

(56) References Cited

U.S. PATENT DOCUMENTS

| 4,384,359 | A | 5/1983 | Franke |
| 4,991,190 | A | 2/1991 | Mori |
| 6,421,412 | B1 * | 7/2002 | Hsieh et al. ................. 378/9 |
| 6,426,987 | B2 * | 7/2002 | Nakamura et al. ............ 378/4 |
| 6,504,893 | B1 | 1/2003 | Flohr et al. |
| 2005/0089134 | A1 | 4/2005 | Bruder et al. |
| 2007/0237286 | A1 * | 10/2007 | Imai ............................. 378/4 |

FOREIGN PATENT DOCUMENTS

| DE | 2951222 A1 | 6/1981 |
| DE | 19957082 A1 | 8/2001 |
| DE | 10302565 A1 | 8/2004 |

* cited by examiner

*Primary Examiner*—Hoon Song
(74) *Attorney, Agent, or Firm*—Harness, Dickey & Pierce, P.L.C.

(57) ABSTRACT

At least one embodiment of the present invention relates to a CT scanner and/or a method for helical scanning of an examination object which has at least one portion undergoing periodic motion. In at least one embodiment, the CT scanner includes at least one bearing apparatus, arranged along a system axis of the CT scanner, for bearing the examination object, two scanning systems which can rotate around the system axis and which are arranged coaxially, respectively having a focus from which a beam can be emitted and a flat-design detector array, arranged opposite the respective focus, including a multiplicity of distributed detector elements which can detect the rays of the beam, wherein projection data can be generated by the scanning systems which represents the attenuation of the rays while traversing the examination object, and wherein the bearing apparatus and/or the scanning systems can be displaced along the system axis, a first device/module, preferably an EKG, which can detect and store rest and movement phases of the examination object which has at least one portion undergoing periodic motion in the form of measurement data, and a second device/module which can, based on the measurement data and/or data derived therefrom, trigger and/or control a displacement of the scanning systems and/or the bearing apparatus along the system axis.

27 Claims, 2 Drawing Sheets

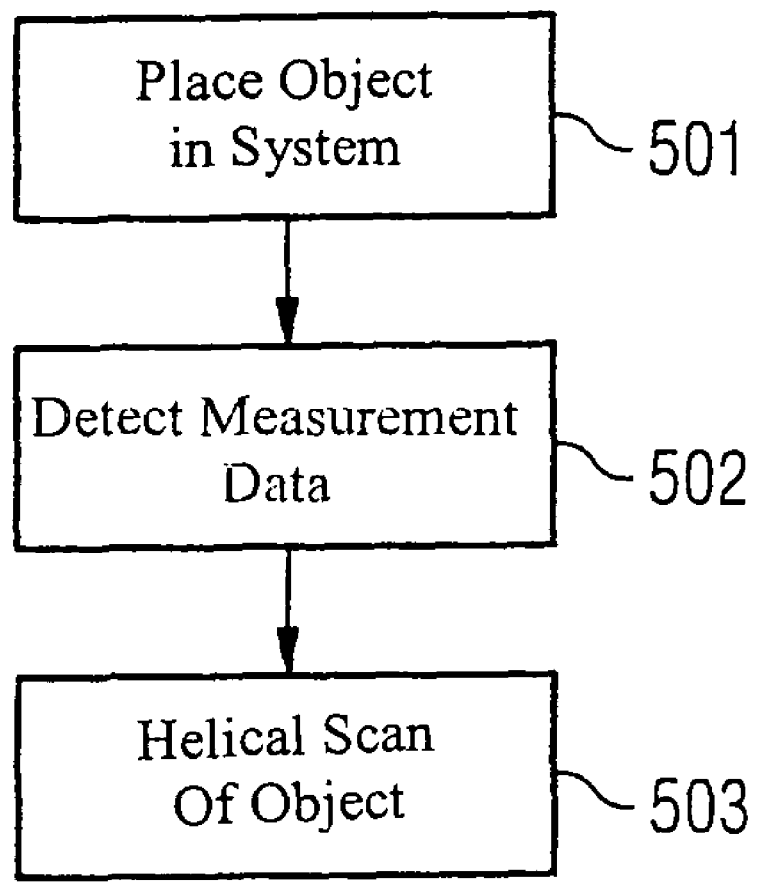

CT SCANNER AND METHOD FOR HELICAL SCANNING OF AN EXAMINATION OBJECT WHICH HAS AT LEAST ONE PORTION UNDERGOING PERIODIC MOTION

PRIORITY STATEMENT

The present application hereby claims priority under 35 U.S.C. §119 on German patent application number DE 10 2007 056 801.2 filed Nov. 23, 2007, the entire contents of which is hereby incorporated herein by reference.

FIELD

Embodiments of the present invention generally relate to a CT scanner and/or a method for helical scanning of an examination object which has at least one portion undergoing periodic motion. Embodiments of the CT scanner and the method additionally permit rapid volume scanning of the examination object with a high temporal resolution.

BACKGROUND

It is well known that CT scanners irradiate an examination object with x-rays, and the attenuation of the x-rays along their path from the radiation source (x-ray source) to the detector system (x-ray detector) is detected. The attenuation is caused by the irradiated materials in the beam path, and hence the attenuation can be understood to be the line integral over the attenuation coefficient of all volume elements (voxels) along the beam path. The projection data detected cannot be interpreted directly; that is to say they do not provide an image of the irradiated layer of the examination object. Only the use of reconstruction methods affords the possibility of back-calculating the attenuation coefficient $\mu$ of the individual voxels from the projected attenuation data and hence generating an image of the distribution of the attenuation coefficients. This affords a much more sensitive examination of the examination object than by only examining projection images.

The so-called CT number is generally used for the purposes of displaying the attenuation distribution rather than using the attenuation coefficient $\mu$ itself; the CT value is a value normalized with respect to the attenuation coefficient of water. The CT number can be calculated from an up to date attenuation coefficient $\mu$, determined by the measurement, by way of the following equation:

$$C = 1000 \times \frac{\mu - \mu_{H_2O}}{\mu_{H_2O}} [HU],$$

where the CT number C is in Hounsfield units [HU]. Water has a value $C_{H_2O}=0$ HU, and air has a value of $C_L=-1000$ HU. Since both representations can be transformed into one another, or are equivalent, the chosen general terms attenuation value or attenuation coefficient are used for both the attenuation coefficient $\mu$ and the CT value.

Modern x-ray computed tomography scanners (CT scanners) are used for recording, evaluating, and displaying the three-dimensional attenuation distribution. A CT scanner typically comprises a radiation source which directs a collimated, pyramid-shaped or fan-shaped beam from a focus through the examination object, e.g. a patient, and onto a detector system made up from a number of detector elements. Depending on the design of the CT scanner, the radiation source and the detector system are attached to, for example, a gantry or a C-arm which can be rotated through an angle $\alpha$ around a system axis (z-axis). Furthermore, provision is made for a bearing device for the examination object which can be moved or displaced along the system axis (z-axis). During the recording, each detector element of the detector system hit by the radiation produces a signal which represents a measure of the overall transparency of the examination object to the radiation emitted by the radiation source on its way to the detector system, or it represents the corresponding radiation attenuation. The set of output signals of the detector elements of the detector system obtained for a particular position of the radiation source is referred to as a projection. The position from which the beam is transmitted through the examination object is continually changed as a result of the rotation of the gantry/C-arm. A so-called scan comprises a multiplicity of projections obtained at different positions of the gantry/C-arm and/or at different positions of the bearing device. A distinction is made between sequential scanning methods (axial scan operation) and helical scanning methods.

As described above, a two-dimensional slice image of a layer of the examination object is reconstructed on the basis of a data record generated during a scan. The quantity and quality of the measurement data detected during a scan depends on the type of detector system used. It is possible to simultaneously record a number of layers using a detector system comprising an array of a number of rows and columns of detector elements. Nowadays, detector systems having 256 or more rows are known.

There are problems reconstructing the projection data if the examination object moves during the scan described above; that is to say if it moves during the detection of the projection data. Scanning a beating heart is particularly affected by this problem. Distracting movement artifacts occur in the subsequent reconstruction of the obtained projection data as a result of movements of the examination object or a portion thereof during the scan.

So as to minimize such movement artifacts, CT scanners, such as those disclosed in U.S. Pat. No. 4,991,190 and DE 29 51-222 A1, are known which comprise two scanning systems, with a scanning system in each case comprising a radiation source or a focus, and a detector system. The advantages of such CT scanners, disclosed in those documents, compared to a CT scanner comprising only one scanning system lie in the possibility of examining an examination object with an increased scanning speed or with an increased scan resolution.

High scanning speeds are particularly advantageous if movement artifacts in the reconstructed image are intended to be minimized. A high scanning speed ensures that all projections from different rotation angle positions $\alpha$, used to reconstruct an image, as far as possible detect the same movement state of an object, for example the same cardiac phase of heart beats. In known CT scanners, the two scanning systems are arranged around a common rotational axis and are arranged offset to one another by an angle of 90 degrees in the direction of rotation so that the scanning speed can be doubled when suitable reconstruction methods are used.

However, CT scanners with a plurality of scanning systems can also be used to generate images with a higher resolution. For this purpose, the scanning systems are arranged around the common rotational axis so that, in the case of an identical projection direction, the projections of the two scanning systems are offset with respect to one another by a distance which is less than one detector element. A higher resolution image can be calculated by evaluating the projections detected by the scanning systems at successive times from the respective projection directions. A higher resolution is advantageous for examining blood vessels, for example, where small examination volumes have to be scanned.

The projections for reconstructing an image generated by both scanning systems are processed together in both the increased scanning speed mode and the increased scan resolution mode. The data is processed knowing the system angle which, is formed in the azimuthal direction between the scanning systems arranged around a common rotational axis.

SUMMARY

In at least one embodiment of the invention, a CT scanner and/or a method are specified for helical scanning of an examination object which has at least one portion undergoing periodic motion, and, in the process, to increase the functionality of present CT scanners and methods. The CT scanner and the method are intended to be particularly suitable for helical scanning of a beating heart.

The CT scanner according to at least one embodiment of the invention for helical scanning of an examination object which has at least one portion undergoing periodic motion comprises at least one bearing apparatus, arranged along a system axis (z-axis) of the CT scanner, for bearing the examination object, two scanning systems which can rotate around the system axis (z-axis) and which are arranged coaxially, respectively having a focus from which a beam can be emitted and a flat-design detector array, arranged opposite the respective focus, comprising a multiplicity of distributed detector elements which can detect the rays of the beam, wherein projection data can be generated by the scanning systems which represents the attenuation of the rays while traversing the examination object, and wherein the bearing apparatus and/or the scanning systems can be displaced along the system axis (z-axis).

The CT scanner according to at least one embodiment of the invention furthermore comprises a first device/module which can detect and store rest and movement phases of the examination object which has at least one portion undergoing periodic motion in the form of measurement data, and a second device/module which can, based on the measurement data and/or data derived therefrom, trigger and/or control a displacement of the scanning systems and/or the bearing apparatus along the system axis (z-axis) before and/or during the helical scanning of the examination object.

In the present case, the CT scanner according to at least one embodiment of the invention is only operated in the helical scanning mode and it is particularly suitable for helical scanning of a beating heart of a living human or animal. Here, the scanning systems are preferably coplanar and/or offset by 90 degrees with respect to one another in the direction of rotation.

For the purposes of detecting the rest and movement phases of the examination object which has at least one portion undergoing periodic motion, the first device/module can comprise mechanical, optical, electrical, electromagnetic, magnetic or chemical sensors known to the person skilled in the art. However, the first device/module is preferably designed to detect measurement data from an electrocardiogram (EKG) so that the rest and movements phases of a beating heart can be detected as an electrocardiogram. For this purpose, appropriate sensors are attached to the patient and they can be connected to the first device/module. The first device/module can be designed as a stand-alone device which can be connected to a control unit of the CT scanner, or it can, for example, be integrated into a control unit of the CT scanner, with the operation of the CT scanner including the bearing apparatus being able to be controlled by the control unit. Additionally, the most diverse arrangements or embodiments of the first device, which relate to a design optimized for a desired examination purpose and which lie within the scope of the ability of a person skilled in the art, are feasible.

The second device/module is preferably housed in the control unit of the CT scanner. It can preferably be designed as a software module and implemented in the control equipment.

In an example embodiment of the CT scanner, extrapolated data about future rest and movement phases of the examination object can be determined by the second device/module. The extrapolation is based on the detected measurement data, for example the patient EKG, with extrapolation of the measurement data being carried out by way of known mathematical methods. Furthermore, the displacement of the scanning systems and/or the bearing apparatus along the system axis (z-axis) can be triggered and/or controlled by the second device/module on the basis of the determined extrapolated data. In this context, triggering refers to starting the displacement movement of the scanning systems and/or the bearing apparatus along the system axis (z-axis), for example at the moment at which prescribable conditions are satisfied (a certain time is reached or a particular phase angle is present, etc.). The term control refers to controlling the displacement movement after the latter's start. In this respect, controlling can include setting certain velocity profiles or changes in the velocity of the displacement velocity depending on prescribable conditions. However, the helical scanning is typically conducted at a constant displacement velocity.

In a further example embodiment of the CT scanner, the displacement of the scanning systems and/or the bearing apparatus can be triggered and/or controlled by the second device/module in such a fashion that the helical scanning of the examination object which has at least one portion undergoing periodic motion is carried out during a prescribable rest or movement phase of the latter.

In order to completely scan e.g. a beating heart of a patient during a prescribed cardiac phase using the CT scanner according to at least one embodiment of the invention, future heart beats are prospectively estimated using a patient EKG after detecting the patient EKG; that is to say they are extrapolated from the detected patient EKG data. Furthermore, the displacement of the scanning systems and/or the bearing apparatus along the system axis (z-axis) is triggered or controlled on the basis of the extrapolated EKG data so that helical scanning of the entire heart is possible in the prescribed part of the cardiac phase without significant movements of the heart occurring during the helical scanning. In the case of a sufficient detector aperture, preferably having an aperture of 64×0.6 mm or larger, the displacement of the scanning systems and/or the bearing apparatus along the system axis (z-axis) can be carried out so quickly that reconstructing the projection data detected during a prescribed rest or movement phase of the heart is possible without any significant movement artifacts. For this purpose, the scanning systems and/or the bearing apparatus can in particular be displaced along the system axis (z-axis) at such a velocity that imaging in a prescribable part of the phase, for example the end-diastolic phase, of a heart beat can be implemented. In the case of helical scans, either the scanning systems or the bearing apparatus are typically displaced along the system axis (z-axis), depending on the design of the CT scanner. However, a correspondingly tuned simultaneous displacement of the scanning systems and bearing apparatus along the system axis (z-axis) is feasible in principle. In contrast to known gated cardio-reconstructions, the cardiac phase is, in the present case, a function of the image position.

The scanning systems or the bearing apparatus can, after an appropriate acceleration phase, preferably be displaced along the system axis (z-axis) with a pitch value p≧3 or with a constant velocity v≧50 cm/s. In the case of helical scanning, the pitch value specifies the ratio of the feed of the bearing apparatus or the examination region per gantry rotation and the layer thickness of the detector. For example, in the case of helical scanning of an examination region having, for example, a diameter of 250 mm, a maximum pitch value of 1.7 can be achieved without projection gaps occurring within the examination region when using only a single scanning system with the cone angle (focus angle) of the x-rays being set to approximately 20 degrees in order to irradiate a 32-row detector with detector element lengths of in each case 0.6 mm. If, as in the present case, CT scanners having two or more scanning systems are used, then the helical scanning can be conducted with a significantly higher pitch value, for example ≧3. Hence, a CT scanner with two scanning systems can carry out helical scanning with a significantly higher feed than the conventional helical CT with only one scanning system. However, the displacement velocity is bounded above by that velocity at which projection gaps occur during helical scanning.

The time interval during the displacement along the system axis (z-axis) for mechanical acceleration or deceleration of the scanning systems or the bearing apparatus to the velocity values specified above typically corresponds to a helical speed-up phase or helical slow-down phase of ⅛ of a rotation of the scanning systems. Due to this speed-up or slow-down phase, the patient dose during, for example, a cardiac record can increase by approximately 25%. Advantageously, provision is made for a moveable shield on the CT scanner which, during the speed-up and slow-down phase, shields the detector rows not required in the reconstruction, and thus significantly reduces this additional dose.

In a further embodiment, provision is made in the CT scanner for a third device/module which can process the generated projection data into tomographic slice images and/or a 3D image data record using image reconstruction. Partial images from quarter rotation data records acquired in parallel can preferably be combined for the image reconstruction by the third device/module.

The CT scanner according to at least one embodiment of the invention affords the possibility of, for example, a movement free display of the coronary vessels during only one heart beat and thus extends the functionality of current CT scanners in an outstanding manner.

The method according to at least one embodiment of the invention for helical scanning of an examination object which has at least one portion undergoing periodic motion using a CT scanner comprises the following method steps:

Firstly, the provision of a CT scanner with at least one bearing apparatus, arranged along a system axis (z-axis) of the CT scanner, for bearing the examination object, two scanning systems which can rotate around the system axis (z-axis) and which are arranged coaxially, respectively having a focus from which a beam can be emitted and a flat-design detector array, arranged opposite the respective focus, comprising a multiplicity of distributed detector elements which can detect the rays of the beam, wherein projection data can be generated by the scanning systems which represents the attenuation of the rays while traversing the examination object, and wherein the bearing apparatus and/or the scanning systems can be displaced along the system axis (z-axis).

Secondly, the detection of rest and movement phases of the examination object which has at least one portion undergoing periodic motion as measurement data, preferably in the form of measurement data from an electrocardiogram (EKG), and storage of the detected measurement data.

Thirdly, helical scanning of the examination object, wherein a displacement of the bearing apparatus and/or of the scanning systems along the system axis (z-axis) is triggered and/or controlled on the basis of the detected data and/or the data derived therefrom.

In a particularly advantageous manner, in a development of at least one embodiment of the method, extrapolated data about future rest and movement phases of the examination object which has at least one portion undergoing periodic motion is determined on the basis of the detected measurement data, and the displacement of the scanning systems and/or the bearing apparatus along the system axis (z-axis) is triggered and/or controlled on the basis of the determined extrapolated data.

In a further particularly advantageous alternative of at least one embodiment of the method, a rest or movement phase of the examination object which has at least one portion undergoing periodic motion is prescribed during which the helical scanning is intended to be carried out. Moreover, in this alternative of the method, the displacement of the scanning systems and/or the bearing apparatus is triggered and/or controlled in such a fashion that the complete helical scanning of the examination object which has at least one portion undergoing periodic motion is carried out during the prescribable rest or movement phase.

The displacement of the scanning systems and/or the bearing apparatus along the system axis (z-axis) typically comprises an acceleration phase, a phase at constant displacement velocity during which the examination object is scanned, and a deceleration phase. The scanning systems or the bearing apparatus are mechanically accelerated to the intended velocity during the acceleration phase. Conversely, they are correspondingly mechanically braked during the deceleration phase. However, in principle, the displacement motion can have any velocity profile during the scan so that a number of acceleration and deceleration phases can be present.

As already mentioned above, after an acceleration phase, the scanning systems or the bearing apparatus are preferably displaced along the system axis (z-axis) at a constant displacement velocity with a pitch value p≧3 or at a constant velocity v≧50 cm/s. In the case of helical scanning of a beating heart during a prescribable rest or movement phase of the heart, the scanning systems and/or the bearing apparatus can be displaced along the system axis (z-axis) at such a velocity that imaging can be implemented during a desired phase of a heart beat, e.g. during the end-diastolic phase.

Finally, in accordance with at least one embodiment, the CT scanner can be used for a motion-free display of coronary vessels of a beating heart during only one heart beat.

BRIEF DESCRIPTION OF THE DRAWINGS

Example embodiments of the invention and further advantageous refinements of the invention in accordance with the dependent claims are illustrated in the following schematic drawings, in which:

FIG. 2 shows a procedure according to an embodiment of the invention.

DETAILED DESCRIPTION OF THE EXAMPLE EMBODIMENTS

Figure 1:
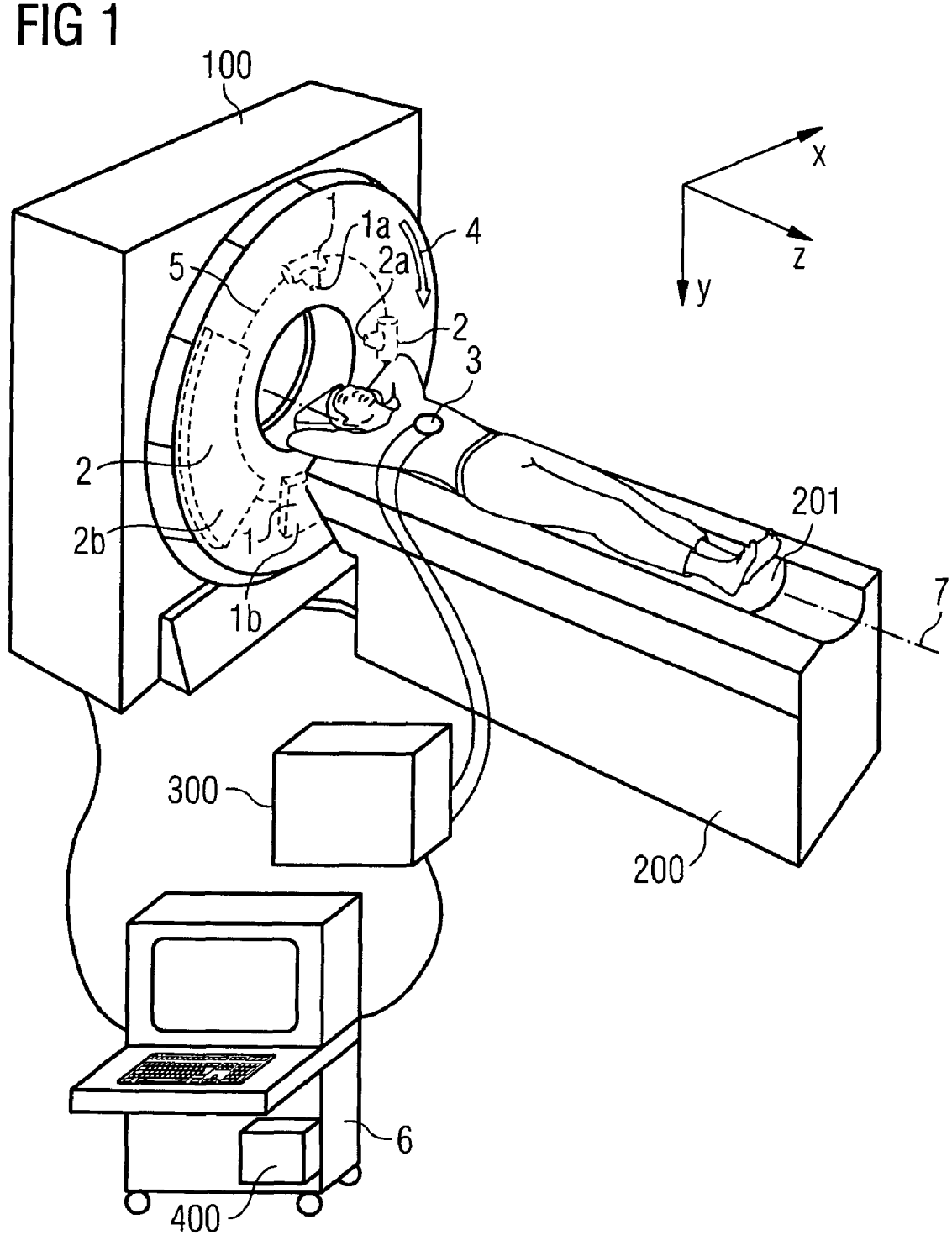
FIG. 1 shows a CT scanner according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms' "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a CT scanner according to an embodiment of the invention in a perspective view. The CT scanner 100 comprises a rotatable gantry with two scanning systems 1, 2, a bearing apparatus 200 on which a patient lies, a first device/module 300 which can detect rest and movement phases of the regularly moving patient heart 3 in the form of EKG measurement data, and control equipment 6 comprising a second device/module 400 which can trigger and/or control a displacement of the bearing apparatus along the system axis (z-axis) before and/or during the helical scanning of the patient heart 3 on the basis of the measurement data and/or data derived therefrom. The control equipment 6 is connected to the first device/module 300, the gantry and the scanning systems 1, 2, and the bearing apparatus 200.

The scanning systems 1, 2, arranged rotatably on the gantry, afford the possibility of detecting helical scan projections of the patient heart 3 from a multiplicity of different projection directions. The scanning systems 1, 2 respectively have a focus 1a, 2a, from which a beam can be emitted, and a flat-design detector array 1b, 2b, arranged opposite, with a multiplicity of distributed detector elements by way of which the rays of the beam are detectable. The second scanning system 2 is offset with respect to the first scanning system 1 by an angle of 90 degrees in the shown direction of rotation 4. Both scanning systems 1, 2 are substantially in the same measurement plane 5.

The bearing apparatus 200 is designed with a moveable table top 201 on which the patient is laid down and which can be displaced in the direction of a system axis (z-axis) 7. As a result of this, the patient and his examination region of interest (the heart in the present case) can be moved through an opening in the housing of the CT scanner 100 into the measurement plane 5 of the two scanning systems 1, 2. In this manner, the examination region of the examination object and the two scanning systems 1, 2 can be displaced relative to one another along the system axis (z-axis).

In order to detect projections, the two scanning systems 1, 2 respectively have one emitter in the form of an x-ray tube or a corresponding focus 1a, 2a, and a detector 1b, 2b arranged opposite therefrom, with each detector 1b, 2b comprising a number of detector elements arranged in columns and rows. Each focus generates a ray fan which passes through the respective measurement area of the scanning system 1, 2. The x-ray radiation is subsequently incident on the detector elements of the respective detector 1b, 2b. The detector elements generate an attenuation value depending on the attenuation of the x-ray radiation passing through the respective measurement area of the scanning system 1, 2. The x-ray radiation is in each case converted into an attenuation value by way of, for example, a photodiode optically coupled to a scintillator or a direct-conversion semiconductor. In this fashion, each detector 1b, 2b generates a set of attenuation values which are recorded for a particular projection direction of the scanning system 1, 2.

As described above, the present CT scanner having two scanning systems 1, 2 can attain a significantly higher displacement velocity of the moveable table top 201 without projection gaps occurring than CT scanners with one scanning system. This is used in the present case in order to scan the heart 3 of the patient with a pitch of 3.5. In this case, the detectors 1b, 2b have a detector aperture of 64×0.6 mm; that is to say they respectively have 64 rows and a detector element length of respectively 0.6 mm along the system axis (z-axis).

Firstly, the first module 300 (EKG equipment in the present case) is used to detect and store the rest and movement phases of the heart 3 by measuring the cardiac currents. The appropriate sensors for measuring the cardiac currents are attached to the patient and connected to the first module 300 via electrical lines. The patient EKG detected by the first module 300 is subsequently evaluated by the second module 400. Hence the first module 300 is electrically connected to the second module 400. Based on the detected patient EKG, or the measurement values on which the patient EKG is based, the module 400 extrapolates the future heart beats of the patient.

In order to now make helical scanning of the heart possible during a prescribable region of a heart beat, the displacement of the moveable table top 201 is triggered, that is to say started, on the basis of the extrapolated data of the future heart beats and the prescribed region of the heart beat. In the process, the table top is accelerated to a constant displacement velocity of 50 cm/s.

Projections of the heart 3 to be examined are detected from a multiplicity of different projection directions at different positions along the system axis 7 due to the rotation of the gantry during the constant feed of the table top along the system axis 7. The displacement velocity of 50 cm/s is fast enough to permit, for example, scanning the whole heart in the end-diastolic phase without projection gaps existing. The projections of the two scanning systems 1, 2 obtained in this manner are transmitted to a control and computational unit 6, and processed to form an image.

FIG. 2 schematically reproduces the progression of the method according to an embodiment of the invention for helical scanning of an examination object which has at least one portion undergoing periodic motion using a CT scanner 100. The method comprises three method steps.

Step 501 provides a CT scanner 100 with at least one bearing apparatus 200, arranged along a system axis (z-axis) 7 of the CT scanner 100, for bearing the examination object, two scanning systems 1, 2 which can rotate around the system axis (z-axis) 7 and which are arranged coaxially, respectively having a focus 1a, 2a from which a beam can be emitted and a flat-design detector array 1b, 2b, arranged opposite the respective focus, comprising a multiplicity of distributed detector elements which can detect the rays of the beam, wherein projection data can be generated by the scanning systems 1, 2 which represents the attenuation of the rays while traversing the examination object, and wherein the bearing apparatus 200 or a displaceable table 201 and/or the scanning systems 1, 2 can be displaced along the system axis (z-axis) 7.

In step 502, the rest and movement phases of the examination object which has at least one portion undergoing periodic motion are detected as measurement data, preferably in the form of measurement data from an electrocardiogram (EKG), and the detected measurement data is stored.

Finally, in step 503, helical scanning of the examination object using the CT scanner 100 is carried out, wherein a displacement of the bearing apparatus 200 or a moveable table 201 and/or of the scanning systems 1, 2 along the system axis (z-axis) 7 is triggered and/or controlled on the basis of the detected data and/or the data derived therefrom.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A CT scanner for helical scanning of an examination object which has at least one portion undergoing periodic motion, comprising:
    at least one bearing apparatus, arranged along a system axis of the CT scanner, for bearing the examination object;
    two scanning systems, rotatable around the system axis and arranged coaxially, each respectively having a focus from which a beam is emitable and a flat-design detector array, arranged opposite the respective focus, including a multiplicity of distributed detector elements to detect the rays of the beam, wherein projection data is generatable by the scanning systems which represents attenuation of the rays while traversing the examination object, at least one of the at least one bearing apparatus and the scanning systems are displaceable along the system axis;
    first means for detecting rest and movement phases of the examination object, which has at least one portion undergoing periodic motion in the form of measurement data, the first means for detecting being configured to detect measurement data from an electrocardiogram; and second means for, based on at least one of the detected measurement data and data derived from the detected measurement data, at least one of triggering and controlling a displacement of at least one of the scanning systems and the at least one bearing apparatus along the system axis at least one of before and during the helical scanning of the examination object, wherein the second means is configured to determine extrapolated data about future rest and movement phases of the examination object based on the detected measurement data, and the displacement of at least one of the scanning systems and the at least one bearing apparatus along the system axis is at least one of triggerable and controllable on the basis of the determined extrapolated data.

2. The CT scanner as claimed in claim 1, wherein the displacement of at least one of the scanning systems and the bearing apparatus is triggerable and controllable by the second means in such a fashion that the helical scanning of the examination object which has at least one portion undergoing periodic motion is carried out during a prescribable rest or movement phase of the examination object.

3. The CT scanner as claimed in claim 1, wherein at least one of the scanning systems and the at least one bearing apparatus is displaceable along the system axis with a pitch value $p \geq 3$.

4. The CT scanner as claimed in claim 1, wherein at least one of the scanning systems and the at least one bearing apparatus is, after an acceleration phase, displaceable along the system axis with a constant velocity $v \geq 50$ cm/s.

5. The CT scanner as claimed in claim 1, wherein the examination object is a human and the regularly moving portion is a beating heart of the human.

6. The CT scanner as claimed in claim 5, wherein at least one of the scanning systems and the at least one bearing apparatus is displaceable along the system axis at such a velocity that imaging is implementable during the end-diastolic phase of a heart beat.

7. The CT scanner as claimed in claim 1, further comprising:

third means for processing the generated projection data into at least one tomographic slice images and a 3D image data record using image reconstruction.

8. The CT scanner as claimed in claim 1, wherein detector arrays are provided with an aperture of 64×0.6 mm or larger.

9. The CT scanner as claimed in claim 1, wherein the scanning systems are arranged in a coplanar fashion.

10. The CT scanner as claimed in claim 1, wherein the two scanning systems are arranged offset to one another by 90 degrees in the direction of rotation.

11. The CT scanner as claimed in claim 1, wherein a shield is provided by way of which the detector rows which are not required for the reconstruction can be shielded.

12. The CT scanner as claimed in claim 1, wherein partial images from quarter rotation data records acquired in parallel are combinable for the image reconstruction by the third means.

13. A method, comprising:

using the CT scanner as claimed in claim 1 for a motion-free display of coronary vessels of a beating heart during only one heart beat.

14. The CT scanner as claimed in claim 1, wherein extrapolated data about future rest and movement phases of the examination object are determinable by the second means based on the detected measurement data, and the displacement of at least one of the scanning systems and the at least one bearing apparatus along the system axis is at least one of triggerable and controllable on the basis of the determined extrapolated data.

15. The CT scanner as claimed in claim 14, wherein the displacement of at least one of the scanning systems and the bearing apparatus is triggerable and controllable by the second means in such a fashion that the helical scanning of the examination object which has at least one portion undergoing periodic motion is carried out during a prescribable rest or movement phase of the examination object.

16. The CT scanner as claimed in claim 1, wherein the measurement data is in the form of measurement data from an electrocardiogram (EKG).

17. A method for helical scanning of an examination object which has at least one portion undergoing periodic motion using a CT scanner including at least one bearing apparatus arranged along a system axis of the CT scanner, for bearing the examination object, and two scanning systems, to rotate around the system axis, being arranged coaxially, respectively having a focus from which a beam can be emitted and a flat-design detector array, arranged opposite the respective focus, including a multiplicity of distributed detector elements to detect the rays of the beam, projection data being generatable by the scanning systems which represent attenuation of the rays while traversing the examination object, at least one of the at least one bearing apparatus and the scanning systems being displaceable long the system axis, the method comprising:

detecting rest and movement phases of the examination object, which has at least one portion undergoing periodic motion, as measurement data;

storing the detected measurement data;

helically scanning the examination object using the CT scanner, wherein a displacement of at least one of the bearing apparatus and the scanning systems along the system axis being at least one of triggered and controlled on the basis of at least one of the detected data and data derived from the detected data; and determining extrapolated data about future rest and movement phases of the examination object which has at least one portion undergoing periodic motion on the basis of the detected measurement data, and the displacement of at least one of the scanning systems and the at least one bearing apparatus alone the system axis is triggered and controlled on the basis of the determined extrapolated data.

18. The method as claimed in claim 17, wherein a rest or movement phase of the examination object which has at least one portion undergoing periodic motion is prescribed during which the helical scanning is intended to be carried out, and the displacement of at least one of the scanning systems and the at least one bearing apparatus is at least one of triggered and controlled in such a fashion that the helical scanning of the examination object which has at least one portion undergoing periodic motion is carried out during the prescribable rest or movement phase.

19. The method as claimed in claim 17, wherein the displacement of at least one of the scanning systems and the at least one bearing apparatus along the system axis comprises an acceleration phase, a phase at constant displacement velocity, and a deceleration phase.

20. The method as claimed in claim 19, wherein at least one of the scanning systems and the at least one bearing apparatus is displaced along the system axis with a pitch value $p \geq 3$ during the phase of constant displacement velocity.

21. The method as claimed in claim 19, wherein at least one of the scanning systems and the at least one bearing apparatus are displaced along the system axis with a constant velocity v $\geqq$ 50 cm/s during the phase of constant displacement velocity.

22. The method as claimed in claim 19, wherein a shield is provided which shields the detector rows not required for a reconstruction during the acceleration phase and during the deceleration phase.

23. The method as claimed in claim 17, wherein the examination object is a human and the regularly moving portion is his beating heart.

24. The method as claimed in claim 23, wherein at least one of the scanning systems and the at least one bearing apparatus is displaceable along the system axis at such a velocity that imaging is implementable during the end-diastolic phase of a heart beat.

25. The method as claimed in claim 17, wherein the generated projection data are stored and processed into at least one of tomographic slice images and a 3D image data record using image reconstruction.

26. The method as claimed in claim 25, wherein partial images from quarter rotation data records acquired in parallel are combined for the image reconstruction.

27. The method as claimed in claim 17, wherein the measurement data is in the form of measurement data from an electrocardiogram (EKG).

* * * * *